United States Patent
Steffens et al.

(10) Patent No.: US 7,374,660 B2
(45) Date of Patent: May 20, 2008

(54) PROCESS FOR SELECTIVELY PRODUCING $C_3$ OLEFINS IN A FLUID CATALYTIC CRACKING PROCESS WITH RECYCLE OF A $C_4$ FRACTION TO A SECONDARY REACTION ZONE SEPARATE FROM A DENSE BED STRIPPING ZONE

(75) Inventors: Todd R. Steffens, Centreville, VA (US); Brian Erik Henry, Baton Rouge, LA (US); Jacob Johannes Thiart, Baton Rouge, LA (US); Nicole J. Lai, Philadelphia, PA (US); James D. Dearth, Baton Rouge, LA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 557 days.

(21) Appl. No.: 10/993,057

(22) Filed: Nov. 19, 2004

(65) Prior Publication Data
US 2006/0108261 A1    May 25, 2006

(51) Int. Cl.
*C10G 51/02* (2006.01)
*C10G 51/04* (2006.01)
*C10G 55/04* (2006.01)
*C10G 55/06* (2006.01)
*C10G 57/00* (2006.01)
*C10G 9/00* (2006.01)
*C10G 15/00* (2006.01)
*C10G 47/00* (2006.01)

(52) U.S. Cl. .......................... 208/67; 208/104
(58) Field of Classification Search ............ 208/67, 208/104, 120.01; 585/653, 648
See application file for complete search history.

(56) References Cited

U.S. PATENT DOCUMENTS

| | | | |
|---|---|---|---|
| 3,702,886 A | 11/1972 | Argauer et al. | |
| 3,709,979 A | 1/1973 | Chu | |
| 3,770,614 A | 11/1973 | Graven | |
| 3,832,449 A | 8/1974 | Rosinski et al. | |
| 3,948,758 A | 4/1976 | Bonacci et al. | |
| 4,016,245 A | 4/1977 | Plank et al. | |
| 4,076,842 A | 2/1978 | Plank et al. | |
| 4,229,424 A | 10/1980 | Kokotailo | |
| 4,254,297 A | 3/1981 | Frenken et al. | |
| 4,310,440 A | 1/1982 | Wilson et al. | |
| 4,440,871 A | 4/1984 | Lok et al. | |
| 4,500,651 A | 2/1985 | Lok et al. | |
| 5,164,071 A * | 11/1992 | Harandi .................. | 208/67 |
| 5,730,859 A * | 3/1998 | Johnson et al. ............. | 208/78 |
| 6,093,867 A | 7/2000 | Ladwig et al. | |
| 6,222,087 B1 * | 4/2001 | Johnson et al. ............ | 585/651 |
| 6,388,161 B1 * | 5/2002 | Dath et al. ................. | 585/648 |
| 6,489,530 B1 * | 12/2002 | Stuntz ....................... | 585/648 |

FOREIGN PATENT DOCUMENTS

EP      A 229295      7/1987

OTHER PUBLICATIONS

Anderson et al., Reactions on ZSM-5Type Zeolite Catalysts, v. 58, 1979, pp. 114-130.

* cited by examiner

*Primary Examiner*—Walter D. Griffin
*Assistant Examiner*—Frank C Campanell

(57) ABSTRACT

A process for selectively producing $C_3$ olefins from a catalytically cracked or thermally cracked naphtha stream is disclosed herein. The naphtha stream is introduced into a process unit comprised of a reaction zone, a stripping zone containing a dense phase, a catalyst regeneration zone, and a fractionation zone. The naphtha feedstream is contacted in the reaction zone with a catalyst containing from about 10 to about 50 wt. % of a crystalline zeolite having an average pore diameter less than about 0.7 nanometers at reaction conditions. Vapor products are collected overhead and the catalyst particles are passed through the stripping zone on the way to the catalyst regeneration zone. Volatiles are stripped with steam in the stripping zone and the catalyst particles are sent to the catalyst regeneration zone where coke is burned from the catalyst, and are then recycled to the reaction zone. Overhead products from the reaction zone are passed to a fractionation zone where a stream of $C_3$ products is recovered and a stream rich in $C_4$ olefins is recycled to a dilute phase reaction zone in the stripping zone separate from the dense phase of the stripping zone. The olefins can be further processed and polymerized to form a variety of polymer materials.

15 Claims, No Drawings

PROCESS FOR SELECTIVELY PRODUCING $C_3$ OLEFINS IN A FLUID CATALYTIC CRACKING PROCESS WITH RECYCLE OF A $C_4$ FRACTION TO A SECONDARY REACTION ZONE SEPARATE FROM A DENSE BED STRIPPING ZONE

FIELD OF THE INVENTION

The present invention relates to a process for producing propylene from a naphtha stream.

BACKGROUND

The need for low emissions fuels has created an increased demand for light olefins used in alkylation, oligomerization, and MTBE and ETBE synthesis processes. In addition, a low-cost supply of light olefins, particularly propylene, continues to be in demand to serve as feedstock for polyolefin production, particularly polypropylene production.

Fixed bed processes for light paraffin dehydrogenation have recently attracted renewed interest for increasing olefin production. However, these types of processes typically require relatively large capital investments and high operating costs. It is therefore advantageous to increase olefin yield using processes with relatively small capital investment. It would be particularly advantageous to increase light olefin yield in catalytic cracking processes so that the olefins could be further processed into polymers such as polypropylene.

A problem inherent in producing olefins products using fluidized catalytic cracking (FCC) units is that the process depends on a specific catalyst balance to maximize production of light olefins while also achieving high conversion of the feed components boiling in the 650° F.+ (about 340° C.+) range. In addition, even if a specific catalyst balance can be maintained to maximize overall olefin production, olefin selectivity is generally low because of undesirable side reactions, such as extensive cracking, isomerization, aromatization, and hydrogen transfer reactions. Light saturated gases produced from undesirable side reactions result in increased costs to recover the desirable light olefins. Therefore, it is desirable to maximize olefin production in a process that allows a high degree of control over the selectivity of $C_3$ and $C_4$ olefins.

SUMMARY OF THE INVENTION

One embodiment of the present invention is a process for producing propylene comprising the steps of (a) feeding a naphtha stream comprising from about 5 to about 40 wt. % paraffins and from about 15 to about 70 wt. % olefins and co-feeding a stream comprising $C_4$ olefins to a process unit comprising a primary reaction zone, a stripping zone, a catalyst regeneration zone, and a fractionation zone; (b) contacting the naphtha stream with a fluidized catalyst in the reaction zone to form a cracked product, the catalyst comprising a zeolite having an average pore diameter of less than about 0.7 nm, and wherein the reaction zone is operated at a temperature from about 500 to about 650° C., a hydrocarbon partial pressure of about 10 to about 40 psia (about 70 to about 280 kPa), a hydrocarbon residence time of about 1 to about 10 seconds, and a catalyst to naphtha feed weight ratio between about 4 and about 10, thereby producing a reaction product wherein no more than about 20 wt. % of paraffins are converted to olefins and wherein propylene comprises at least about 90 mol. % of the total $C_3$ products; (c) passing the catalyst through said stripping zone; (d) passing the stripped catalyst from the stripping zone to the catalyst regeneration zone where the catalyst is regenerated in the presence of an oxygen-containing gas and optionally heated by the combustion of an auxiliary fuel; (e) recycling the regenerated catalyst to the reaction zone; (f) fractionating the cracked product to produce a $C_3$ fraction, a $C_4$ fraction rich in olefins, and optionally a $C_5$ fraction rich in olefins; and recycling at least a portion of the $C_4$ fraction to a dilute phase secondary reaction zone above the dense bed stripping zone.

In another embodiment of the present invention the catalyst is a ZSM-5 type catalyst.

In still another embodiment of the present invention at least a portion of a $C_5$ fraction rich in olefins is recycled to the reaction zone, or to a secondary reaction zone above the dense bed stripping zone, or a combination thereof.

In yet another embodiment of the present invention a $C_4$ olefin stream from another refinery process unit is co-fed with the naphtha fed to the reaction zone or fed to a reaction zone separate from the dense bed stripping zone, or a combination thereof.

In still another embodiment, a separate reaction zone can be a dilute phase reaction zone immediately above a dense phase stripping zone or a separate contacting region which allows control of catalyst contacting at or near the preferred catalytic severity, i.e. about 5 to about 50 weight hourly space velocity (WHSV), preferably about 10 to about 20 WHSV.

In another embodiment of the present invention the feedstock contains about 10 to about 30 wt. % paraffins, and from about 20 to about 70 wt. % olefins.

In another embodiment of the present invention the reaction zone is operated at a temperature from about 525 to about 600° C.

DETAILED DESCRIPTION OF THE INVENTION

Feedstreams that are suitable for producing the relatively high $C_2$, $C_3$, and $C_4$ olefin yields are those streams boiling in the naphtha range and containing from about 5 wt. % to about 40 wt. %, preferably from about 5 wt. % to about 35 wt. % more preferably from about 10 wt. % to about 30 wt. %, and most preferably from about 10 to about 25 wt. % paraffins, and further containing from about 15 wt. %, preferably from about 20 wt. %, to about 70 wt. % olefins. The feed may also contain naphthenes and aromatics. Naphtha boiling range streams are typically those having a boiling range from about 65 to about 430° F. (about 18 to about 225° C.), preferably from about 65 to about 300° F. (about 18 to about 150° C.).

The naphtha can be a thermally cracked or a catalytically cracked naphtha. The naphtha streams can be derived from the fluid catalytic cracking (FCC) of gas oils and resids, or they can be derived from delayed or fluid coking of resids. Preferably, the naphtha streams used in the practice of the present invention derive from the fluid catalytic cracking of gas oils and resids. FCC naphthas are typically rich in olefins and relatively lean in paraffins. It is within the scope of the instant invention to feed or co-feed other olefinic streams that are not catalytically- or thermally-cracked naphthas into said reaction zone with the primary feed. It is believed that this will increase the yield of propylene.

The process of the present invention is performed in a process unit comprising a primary reaction zone (riser), a stripping zone, a catalyst regeneration zone, and a fractionation zone. The stripping zone will typically contain a dense bed of catalyst particles where stripping of volatiles takes place. There will also be space above the dense phase stripping zone wherein the catalyst density is substantially lower. This lower density section of the stripping zone is sometimes referred to herein as the secondary reaction zone. This secondary reaction zone will be separate from the primary reaction zone and also from the dense phase stripping zone.

The naphtha feed is injected into the riser where it contacts a source of hot, regenerated catalyst. The hot catalyst cracks the feed at a temperature from about 500 to about 650° C., preferably from about 525 to about 600° C. The products are separated from the catalyst and sent to a fractionator. The catalyst passes through the stripping zone where a stripping medium, such as steam, strips volatiles from the catalyst particles. As previously mentioned, there will be a dilute phase region between the separation device and the dense phase stripping zone. It is preferred that the stripping medium flow counter to the down flowing catalyst particles.

The stripping can be performed under low-severity conditions to retain a greater fraction of adsorbed hydrocarbons for heat balance. The stripped catalyst is then passed to the regeneration zone where it is regenerated by burning coke on the catalyst in the presence of an oxygen-containing gas, preferably air. Supplemental heat required for providing the heat of reaction and sensible heat in excess of that available from combusting the coke on the catalyst can be provided by direct contact auxiliary fuel combustion. This regeneration step restores catalyst activity and simultaneously heats the catalyst to a temperature from about 650 to about 750° C. The hot regenerated catalyst is then recycled to the reaction zone to crack fresh naphtha feed. Flue gas formed by burning coke and auxiliary fuel in the regenerator may be treated for removal of particulates and for conversion of carbon monoxide. The products from the reaction zone are sent to a fractionation zone where various products are recovered, particularly a $C_3$ fraction, a $C_4$ fraction, and optionally a $C_5$ fraction. The $C_4$ fraction and the $C_5$ fraction will typically be rich in olefins. At least a portion of the $C_4$ fraction can be recycled to a reaction zone above the dense phase stripping zone, which zone will be separate from the dense phase stripping zone. It has unexpectedly been found that it is beneficial to recycle at least a portion of the $C_4$ fraction to a space above the stripping zone. For example, the $C_4$ conversion is higher for injection into the secondary reaction zone above the dense phase stripping zone than for injection into the reaction zone. The yields of propane and other undesirable secondary products are lower than when the $C_4$'s are injected into the dense phase stripping zone. In other words, the stripping zone presents too severe an environment whereas the reaction zone environment is not severe enough.

It may also be desirable to inject another $C_4$ olefin stream into the reaction zone, the dense phase stripping zone, or dilute phase reaction zone separate from the dense phase stripping zone, or a combination thereof. Such another $C_4$ olefin stream (not to be confused with a $C_4$ fraction recycled from the cracked products of the cracking process) would be derived from one or more suitable sources such as conventional FCC process units, coker process units, steam crackers and other process units that produce $C_4$ olefins streams that can be fed to the cracking unit. In one embodiment, the $C_4$ olefin stream may be a raffinate from a methyl-tert-butyl-ether (MTBE) process as previously described. In another embodiment, the $C_4$ olefin stream injected into the stripper section also preferably comprises at least about 75 wt. % n-butenes, more preferably greater than about 90 wt. % n-butenes. Streams containing lower amounts of n-butenes are also acceptable, especially streams containing a significant amount of diolefins, such as butadiene.

While attempts have been made to increase light olefins yields in the FCC process unit itself, it is preferred that the present invention be embodied in a distinct process unit, as previously described, which receives naphtha from a suitable source in the refinery. The reaction zone is operated at process conditions that will maximize $C_2$ to $C_4$ olefins (particularly propylene) selectivity with relatively high conversion of $C_5+$ olefins. Suitable catalysts used with the present invention contain a crystalline zeolite having an average pore diameter less than about 0.7 nanometers (nm), said crystalline zeolite comprising from about 10 to about 50 wt. % of the total fluidized catalyst composition. It is preferred that the crystalline zeolite be selected from the family of medium-pore size (<0.7 nm) crystalline aluminosilicates, otherwise referred to as zeolites. Of particular interest are the medium-pore zeolites with a silica to alumina molar ratio of less than about 75:1, preferably less than about 50:1, and more preferably less than about 40:1, although some embodiments may incorporate a silica to alumina ratio greater than 40:1. The pore diameter, also referred to as effective pore diameter, is measured using standard adsorption techniques and hydrocarbonaceous compounds of known minimum kinetic diameters. See Breck, *Zeolite Molecular Sieves,* 1974 and Anderson et al., J. Catalysis 58, 114 (1979), both of which are incorporated herein by reference.

Medium-pore size zeolites that can be used in the practice of the present invention are described in "Atlas of Zeolite Structure Types", eds. W. H. Meier and D. H. Olson, Butterworth-Heineman, Third Edition, 1992, which is hereby incorporated by reference. The medium-pore size zeolites generally have a pore size from about 0.5 nm, to about 0.7 nm and include for example, MFI, MFS, MEL, MTW, EUO, MTT, HEU, FER, and TON structure type zeolites (IUPAC Commission of Zeolite Nomenclature). Non-limiting examples of such medium-pore size zeolites, include ZSM-5, ZSM-12, ZSM-22, ZSM-23, ZSM-34, ZSM-35, ZSM-38, ZSM-48, ZSM-50, silicalite, and silicalite 2. The most preferred is ZSM-5, which is described in U.S. Pat. Nos. 3,702,886 and 3,770,614. ZSM-11 is described in U.S. Pat. No. 3,709,979; ZSM-12 in U.S. Pat. No. 3,832,449; ZSM-21 and ZSM-38 in U.S. Pat. No. 3,948,758; ZSM-23 in U.S. Pat. No. 4,076,842; and ZSM-35 in U.S. Pat. No. 4,016,245. All of the above patents are incorporated herein by reference. Other suitable medium-pore size materials include the silicoaluminophosphates (SAPO), such as SAPO-4 and SAPO-11 which is described in U.S. Pat. No. 4,440,871; chromosilicates; gallium silicates; iron silicates; aluminum phosphates (ALPO), such as ALPO-11 described in U.S. Pat. No. 4,310,440; titanium aluminosilicates (TASO), such as TASO-45 described in EP-A No. 229,295; boron silicates, described in U.S. Pat. No. 4,254,297; titanium aluminophosphates (TAPO), such as TAPO-11 described in U.S. Pat. No. 4,500,651; and iron aluminosilicates.

The medium-pore-size zeolites can include "crystalline admixtures" which are thought to be the result of faults occurring within the crystal or crystalline area during the synthesis of the zeolites. Examples of crystalline admixtures of ZSM-5 and ZSM-11 are disclosed in U.S. Pat. No. 4,229,424, which is incorporated herein by reference. The crystalline admixtures are themselves medium-pore-size zeolites and are not to be confused with physical admixtures of zeolites in which distinct crystals or crystallites of different zeolites are physically present in the same catalyst composite or hydrothermal reaction mixtures. It is to be understood that physical admixtures can also be used in the practice of this invention.

The catalysts of the present invention may be held together with an inorganic oxide matrix material component. The inorganic oxide matrix component binds the catalyst components together so that the catalyst product is hard enough to survive interparticle and reactor wall collisions. The inorganic oxide matrix can be made from an inorganic oxide sol or gel which is dried to "bind" the catalyst components together. Preferably, the inorganic oxide matrix is not catalytically active and will be comprised of oxides of silicon and aluminum. It is also preferred that separate alumina phases be incorporated into the inorganic oxide matrix. Species of aluminum oxyhydroxides-g-alumina, boehmite, diaspore, and transitional aluminas such as a-alumina, b-alumina, g-alumina, d-alumina, e-alumina, k-alumina, and r-alumina can be employed. Preferably, the alumina species is an aluminum trihydroxide such as gibbsite, bayerite, nordstrandite, or doyelite. The matrix material may also contain phosphorous or aluminum phosphate.

Process conditions include temperatures from about 500 to about 650° C., preferably from about 500 to about 600° C.; hydrocarbon partial pressures from about 10 to about 40 psia (about 70 to about 280 kPa), preferably from about 20 to about 35 psia (about 140 to about 245 kPa); and a catalyst to naphtha (wt/wt) ratio from about 3 to about 12, preferably from about 4 to about 10, where catalyst weight is total weight of the catalyst composite. Steam may be concurrently introduced with the naphtha stream into the reaction zone, with the steam comprising up to about 50 wt. % of the total feed. Preferably, the naphtha residence time in the reaction zone is less than about 10 seconds, for example from about 1 to 10 seconds. The reaction conditions will be such that at least about 60 wt. % of the $C_5+$ olefins in the naphtha stream are converted to $C_4-$ products and less than about 25 wt. %, preferably less than about 20 wt. % of the paraffins are converted to $C_4-$ products, and that propylene comprises at least about 90 mol. %, preferably greater than about 95 mol % of the total $C_3$ reaction products with the weight ratio of propylene to total $C_2-$ products greater than about 3.5.

Preferably, ethylene comprises at least about 90 mol. % of the $C_2$ products, with the weight ratio of propylene:ethylene being greater than about 4. Preferably, the "full range" $C_5+$ naphtha product is enhanced in both motor and research octanes relative to the naphtha feed. It is within the scope of this invention to pre-coke the catalysts before introducing the feed to further improve the selectivity to propylene. It is also within the scope of this invention to feed an effective amount of single-ring aromatics to the reaction zone to also improve the selectivity of propylene versus ethylene. The aromatics may be from an external source such as a reforming process unit or they may consist of heavy naphtha recycle product from the instant process.

The following examples are presented for illustrative purposes only and are not to be taken as limiting the present invention in any way.

EXAMPLES 1-13

The following examples illustrate the impact of process operating conditions on propylene purity with samples of cat naphtha cracked over ZCAT-40 (a catalyst that contains ZSM-5), which had been steamed at 1500° F. (about 815° C.) for 16 hours to simulate commercial equilibrium. Comparison of Examples 1 and 2 show that increasing catalyst to oil wt./wt. ratio improves propylene yield, but sacrifices propylene purity. Comparison of Examples 3 and 4 and 5 and 6 shows reducing oil partial pressure greatly improves propylene purity without compromising propylene yield. Comparison of Examples 7 and 8 and 9 and 10 shows increasing temperature improves both propylene yield and purity. Comparison of Examples 11 and 12 shows decreasing catalyst residence time improves propylene yield and purity. Example 13 shows an example where both high propylene yield and purity are obtained at a reactor temperature and catalyst:oil ratio that can be achieved using a conventional FCC reactor/regenerator design for the second stage.

TABLE 1

| Example | Feed Olefins, wt % | Temp. ° C. | Cat/Oil, wt./wt. | Oil, psia | Oil Res. Time, sec | Cat Res. Time, sec | Wt. % $C_3^-$ | Wt. % Propane | Propylene Purity, % |
|---|---|---|---|---|---|---|---|---|---|
| 1 | 38.6 | 566 | 4.2 | 36 | 0.5 | 4.3 | 11.4 | 0.5 | 95.8% |
| 2 | 38.6 | 569 | 8.4 | 32 | 0.6 | 4.7 | 12.8 | 0.8 | 94.1% |
| 3 | 22.2 | 510 | 8.8 | 18 | 1.2 | 8.6 | 8.2 | 1.1 | 88.2% |
| 4 | 22.2 | 511 | 9.3 | 38 | 1.2 | 5.6 | 6.3 | 1.9 | 76.8% |
| 5 | 38.6 | 632 | 16.6 | 20 | 1.7 | 9.8 | 16.7 | 1.0 | 94.4% |
| 6 | 38.6 | 630 | 16.6 | 13 | 1.3 | 7.5 | 16.8 | 0.6 | 96.6% |
| 7 | 22.2 | 571 | 5.3 | 27 | 0.4 | 0.3 | 6.0 | 0.2 | 96.8% |
| 8 | 22.2 | 586 | 5.1 | 27 | 0.3 | 0.3 | 7.3 | 0.2 | 97.3% |
| 9 | 22.2 | 511 | 9.3 | 38 | 1.2 | 5.6 | 6.3 | 1.9 | 76.8% |
| 10 | 22.2 | 607 | 9.2 | 37 | 1.2 | 6.0 | 10.4 | 2.2 | 82.5% |
| 11 | 22.2 | 576 | 18.0 | 32 | 1.0 | 9.0 | 9.6 | 4.0 | 70.6% |
| 12 | 22.2 | 574 | 18.3 | 32 | 1.0 | 2.4 | 10.1 | 1.9 | 84.2% |
| 13 | 38.6 | 606 | 8.5 | 22 | 1.0 | 7.4 | 15.0 | 0.7 | 95.5% |

| Example | Wt. % $C_2^-$ | Wt. % $C_2^-$ | Ratio of $C_3^-$ to $C_2^-$ | Ratio of $C_3^-$ to $C_2^-$ | Wt. % $C_3^-$ |
|---|---|---|---|---|---|
| 1 | 2.35 | 2.73 | 4.9 | 4.2 | 11.4 |
| 2 | 3.02 | 3.58 | 4.2 | 3.6 | 12.8 |
| 3 | 2.32 | 2.53 | 3.5 | 3.2 | 8.2 |
| 4 | 2.16 | 2.46 | 2.9 | 2.6 | 6.3 |
| 5 | 6.97 | 9.95 | 2.4 | 1.7 | 16.7 |
| 6 | 6.21 | 8.71 | 2.7 | 1.9 | 16.8 |

TABLE 1-continued

| | | | | | |
|---|---|---|---|---|---|
| 7 | 1.03 | 1.64 | 5.8 | 3.7 | 6.0 |
| 8 | 1.48 | 2.02 | 4.9 | 3.6 | 7.3 |
| 9 | 2.16 | 2.46 | 2.9 | 2.6 | 6.3 |
| 10 | 5.21 | 6.74 | 2.0 | 1.5 | 10.4 |
| 11 | 4.99 | 6.67 | 1.9 | 1.4 | 9.6 |
| 12 | 4.43 | 6.27 | 2.3 | 1.6 | 10.1 |
| 13 | 4.45 | 5.76 | 3.3 | 2.6 | 15.0 |

$C_2^- = CH_4 + C_2H_4 + C_2H_6$

Examples 1, 2, 7, and 8 show that $C_3^=:C_2^=$ ratios greater than 4 and $C_3^=:C_2^{=31}$ ratios greater than 3.5 can be achieved by selection of suitable reactor conditions.

EXAMPLES 14-17

The cracking of olefins and paraffins contained in naphtha streams (e.g. FCC naphtha, coker naphtha) over small or medium-pore zeolites such as ZSM-5 can produce significant amounts of ethylene and propylene. The selectivity to ethylene or propylene and selectivity to propylene over propane vary as a function of catalyst and process operating conditions. It has been found that propylene yield can be increased by co-feeding steam along with naphtha to the reactor. The catalyst may be ZSM-5 or other small or medium-pore zeolites. Table 2 below illustrates the increase in propylene yield when 5 wt. % steam is co-fed with an FCC naphtha containing 38.8 wt. % olefins. Although propylene yield is increased, the propylene purity is diminished. Thus, other operating conditions may need to be adjusted to maintain the targeted propylene selectivity.

TABLE 2

| Example | Steam Co-feed | Temp. ° C. | Cat/Oil | Oil psia | Oil Res. Time, sec | Cat Res. Time, sec | Wt % Propylene | Wt % Propane | Propylene Purity, % |
|---|---|---|---|---|---|---|---|---|---|
| 14 | No | 630 | 8.7 | 18 | 0.8 | 8.0 | 11.7 | 0.3 | 97.5% |
| 15 | Yes | 631 | 8.8 | 22 | 1.2 | 6.0 | 13.9 | 0.6 | 95.9% |
| 16 | No | 631 | 8.7 | 18 | 0.8 | 7.8 | 13.6 | 0.4 | 97.1% |
| 17 | Yes | 632 | 8.4 | 22 | 1.1 | 6.1 | 14.6 | 0.8 | 94.8% |

EXAMPLES 18-21

ZCAT-40 was used to crack cat cracker naphtha as described for the above examples. The coked catalyst was then used to crack a $C_4$ stream composed of 6 wt. % n-butane, 9 wt. % i-butane, 47 wt. % 1-butene, and 38 wt. % i-butene in a reactor at the temperatures and space velocities indicated in the table below. As can be seen from the results in the table below, a significant fraction of the feed stream was converted to propylene.

TABLE 3

| | WHSV, Hr-1 | | | |
|---|---|---|---|---|
| | 35 | 18 | 12 | 6 |
| Temperature, ° C. | 575 | 575 | 575 | 575 |
| Butylene Conversion wt. % | 53.0 | 65.7 | 69.9 | 77.3 |
| Product Yields, wt. % | | | | |
| Ethylene | 2.4 | 4.7 | 5.9 | 8.8 |
| Propylene | 20.5 | 27.1 | 28.8 | 27.4 |
| Butylenes | 39.7 | 29.0 | 25.5 | 19.2 |

TABLE 3-continued

| | WHSV, Hr-1 | | | |
|---|---|---|---|---|
| | 35 | 18 | 12 | 6 |
| $C_1$-$C_4$ Light Saturates | 18.2 | 19.2 | 19.8 | 22.0 |
| $C_5$+ Products | 19.3 | 20.0 | 20.0 | 22.6 |

EXAMPLES 22-24

Three experiments were run with a cat naphtha in a circulating riser pilot plant containing a reaction zone having a medium pore zeolite catalyst, a stripping zone, a regeneration zone, and a fractionation zone. Example 22 represents the case where a C4 fraction was recycled to the reaction zone. Example 23 represents the case where a C4 fraction was recycled to the dilute phase reaction zone separate from the dense phase stripping zone, and Example 24 represents the case where a C4 fraction was recycled to the dense phase of the stripping zone.

TABLE 4

| | Example | | |
|---|---|---|---|
| | 22 | 23 | 24 |
| | $C_4$ Recycle To Riser | $C_4$ Recycle To Dilute Phase | $C_4$ Recycle To Dense Phase |
| $C_4$ WHSV, hr-1 | 12.6 | 8.2 | 1.7 |
| One-Pass Yields on Recycled $C_4$'s, wt. % | | | |
| $C_1$ + $C_2$ | 1.59 | 8.56 | 9.61 |
| Propylene | 15.55 | 24.80 | 15.35 |
| Propane | 0.20 | 3.05 | 7.25 |
| Butylene | 37.79 | 20.36 | 13.61 |
| Butane | 11.17 | 13.30 | 13.71 |
| | Recycle to Riser | Recycle Dilute Phase | Recycle to Dense Phase |
| Riser Outlet Temperature, ° C. | 580 | 580 | 580 |
| Reactor Pressure, atm | 3.04 | 3.01 | 3.02 |
| Riser Inlet Hydrocarbon Partial Pressure, atm | 1.42 | 1.40 | 1.41 |

TABLE 4-continued

| | | | |
|---|---|---|---|
| Catalyst-to-oil ratio (includes $C_4$ gases when fed to riser) | 8.91 | 9.00 | 8.92 |
| Oil Residence Time in Riser, sec | 3.2 | 3.0 | 3.1 |
| $C_4$ Recycle as Wt % of Total Feed | 12.3 | 12.3 | 12.3 |
| Average Temperature in Dilute Phase, °C. | | 556 | 556 |
| Average Temperature in Dense Phase, °C. | | | 560 |

The feed to the riser was a light cat naphtha that contained 45 wt % olefins. The $C_4$ feed was a blend of $C_4$'s containing 10.7 wt % butanes and 89.3 wt % butylenes that simulated the composition of the $C_4$ recycle stream. The catalyst used was an Olefins Max® catalyst available from Grace/Davison that was comprised of about 25 wt. % ZSM-5 crystal.

As can be seen from the above Table 4, dilute phase injection of the recycle $C_4$ fraction leads to a higher conversion of the $C_4$'s relative to injection into the riser or reaction zone. Further, injection into the dilute phase produces less than half of the propane formed by injection into the dense phase of the stripper. Also, it was unexpectedly found that the propylene yield from dilute phase injection is significantly higher than that from the $C_4$ injection into either the reaction zone or the dense phase of the stripping zone.

Light olefins resulting from the preferred process may be used as feeds for processes such as oligimerization, polymerization, co-polymerization, ter-polymerization, and related processes (hereinafter "polymerization") to form macromolecules. Such light olefins may be polymerized both alone and in combination with other species, in accordance with polymerization methods known in the art. In some cases it may be desirable to separate, concentrate, purify, upgrade, or otherwise process the light olefins prior to polymerization. Propylene and ethylene are preferred polymerization feeds. Polypropylene and polyethylene are preferred polymerization products made therefrom.

What is claimed is:

1. A process for producing propylene comprising the steps of:
   (a) feeding a naphtha stream comprising from about 5 to about 40 wt. % paraffins and from between about 15 to about 70 wt. % olefins to a process unit comprising a reaction zone, a stripping zone having a dense phase and a dilute phase, a catalyst regeneration zone, and a fractionation zone;
   (b) contacting the naphtha stream with a fluidized bed of catalyst in the reaction zone to form a cracked product, the catalyst comprising a zeolite having an average pore diameter of less than about 0.7 nm and wherein the reaction zone is operated at a temperature from about 500 to about 650° C., a hydrocarbon partial pressure of about 10 to about 40 psia, (about 70 to about 280 kPa) and a hydrocarbon residence time of about 1 to about 10 seconds;
   (c) passing the catalyst through said stripping zone;
   (d) passing the stripped catalyst from the stripping zone to the catalyst regeneration zone where the catalyst is regenerated in the presence of an oxygen-containing gas;
   (e) recycling the regenerated catalyst to the reaction zone;
   (f) fractionating the cracked product to produce a $C_3$ fraction containing propylene, a $C_4$ fraction containing olefins, and optionally a $C_5$ fraction containing olefins;
   (g) recycling at least a portion of the $C_4$ fraction containing olefins to a dilute phase secondary reaction zone above and separate from the dense phase stripping zone; and
   (h) optionally separating propylene from the $C_3$ fraction.

2. The process of claim 1 wherein a $C_4$ olefin stream from another process unit is fed into the reaction zone, the stripping zone, a dilute phase secondary reaction zone above and separate from the dense phase stripping zone, or a combination thereof.

3. The process of claim 2 wherein the $C_4$ olefin stream from another process unit is derived from one or more of an MTBE unit, an FCC unit, a steam cracker, or a coker unit.

4. The process of claim 2 wherein the $C_4$ olefin stream from another process unit comprises an MTBE raffinate stream.

5. The process of claim 2 wherein the $C_4$ olefin stream from another process unit is passed to the process unit from a steam cracker.

6. The process of claim 2 wherein the $C_4$ olefin stream from another process unit comprises at least about 75 wt. % n-butenes.

7. The process of claim 1 wherein the crystalline zeolite is selected from medium-pore size zeolites.

8. The process of claim 7 wherein the crystalline zeolite is ZSM-5.

9. The process of claim 8 wherein the reaction temperature is from about 500 to about 600° C.

10. The process of claim 8 wherein at least about 60 wt. % of the $C_5+$ olefins in the feedstream is converted to $C_4-$ products and less than about 25 wt. % of the paraffins are converted to $C_4-$ products.

11. The process of claim 10 wherein propylene comprises at least about 95 mol. % of the total $C_3$ products.

12. The process of claim 11 wherein the weight ratio of propylene to total $C_2-$ products is greater than about 3.5.

13. The process of claim 1 further comprising the step of producing said $C_5$ fraction and recycling at least a portion of said $C_5$ fraction to the reaction zone, the stripping zone, a dilute phase secondary reaction zone above and separate from the dense phase stripping zone, or a combination thereof.

14. The process of claim 1 further comprising the step of polymerizing the propylene to form polypropylene.

15. The process of claim 1 further comprising the step of separating propylene from the $C_3$ fraction and polymerizing the propylene to form polypropylene.

* * * * *